(12) United States Patent
Steier et al.

(10) Patent No.: US 11,975,214 B2
(45) Date of Patent: May 7, 2024

(54) DEVICES UTILIZING FLUORESCENT ENHANCEMENT THERAGNOSIS TECHNOLOGY

(71) Applicant: Designs for Vision, Inc., Bohemia, NY (US)

(72) Inventors: Liviu Steier, Needham, MA (US); Richard E. Feinbloom, New York, NY (US)

(73) Assignee: Designs for Vision, Inc., Bohemia, NY (US)

( * ) Notice: Subject to any disclaimer, the term of this patent is extended or adjusted under 35 U.S.C. 154(b) by 0 days.

(21) Appl. No.: 17/986,537

(22) Filed: Nov. 14, 2022

(65) Prior Publication Data
US 2023/0071207 A1 Mar. 9, 2023

Related U.S. Application Data

(63) Continuation of application No. 17/371,063, filed on Jul. 8, 2021, now Pat. No. 11,497,927, which is a continuation-in-part of application No. 17/070,307, filed on Oct. 14, 2020, now Pat. No. 11,058,888.

(60) Provisional application No. 63/075,438, filed on Sep. 8, 2020.

(51) Int. Cl.
*A61N 5/06* (2006.01)
*A61B 5/00* (2006.01)

(52) U.S. Cl.
CPC .............. *A61N 5/06* (2013.01); *A61B 5/0071* (2013.01); *A61B 5/0077* (2013.01); *A61B 5/684* (2013.01); *A61N 5/0624* (2013.01); *A61B 2562/0233* (2013.01); *A61N 2005/0626* (2013.01); *A61N 2005/0652* (2013.01); *A61N 2005/0662* (2013.01)

(58) Field of Classification Search
CPC .... A61N 2005/0626; A61N 2005/0652; A61N 2005/0662; A61N 5/06–2005/073; A61B 5/0071; A61B 5/0077; A61B 5/684; A61B 2562/0233; A61B 18/20–18/28
See application file for complete search history.

(56) References Cited

U.S. PATENT DOCUMENTS

| | | | | |
|---|---|---|---|---|
| 4,402,311 A | * | 9/1983 | Hattori | A61B 1/00097 600/117 |
| 4,805,027 A | * | 2/1989 | Sluyter | A61B 1/042 396/17 |
| 2002/0045811 A1 | * | 4/2002 | Kittrell | G02B 6/4296 606/7 |
| 2004/0093043 A1 | | 5/2004 | Edel | |

(Continued)

OTHER PUBLICATIONS

European Search Report, application 21185021.9-1126—dated Dec. 8, 2021.

*Primary Examiner* — Jonathan T Kuo
(74) *Attorney, Agent, or Firm* — Law Office of Carl Giordano, PC

(57) ABSTRACT

A plurality of devices that provide examination/diagnosis and/or treatment benefits to a patient are presented. The device including a plurality of light sources that provide for the emission of light in a plurality of wavelength ranges, wherein the plurality of light sources are activated by a sensor, configured to determine a proximity of the device to a patient, to control an application of a voltage to selected one of the plurality of light sources for a predetermined time period.

20 Claims, 11 Drawing Sheets

(56) References Cited

U.S. PATENT DOCUMENTS

| | | |
|---|---|---|
| 2004/0162549 A1 | 8/2004 | Altshuler |
| 2009/0143842 A1 | 6/2009 | Cumbie |
| 2013/0053928 A1 | 2/2013 | Gat |
| 2013/0280671 A1 | 10/2013 | Brawn |
| 2014/0155753 A1 | 6/2014 | McGuire, Jr. |
| 2018/0310829 A1 | 11/2018 | Frangioni |
| 2021/0038304 A1* | 2/2021 | Bukesov .............. A61B 1/0655 |
| 2021/0275028 A1 | 9/2021 | Dumar |

* cited by examiner

US 11,975,214 B2

1

DEVICES UTILIZING FLUORESCENT ENHANCEMENT THERAGNOSIS TECHNOLOGY

CLAIM OF PRIORITY

This application claims, pursuant to 35 USC 120, as a Continuation application, priority to and the benefit of, patent application Ser. No. 17/371,063 filed on Jul. 8, 2021, which claimed, pursuant to 35 USC 120, as a Continuation-in-Part application, priority to and the benefit of the earlier filing date of patent application Ser. No. 17/070,307, filed on Oct. 14, 2020, which claimed, pursuant to 35 USC 119, priority to and the benefit of the earlier filing date, of that provisional patent application filed on Sep. 8, 2020, and afforded Ser. No. 63/075,438, the contents of which are incorporated by reference herein.

FIELD OF THE INVENTION

This invention relates to the field of medical examination/diagnosis and treatment and more particularly to a devices utilizing Fluorescent Enhancement Theragnosis technology in the identification and treatment of medical conditions.

BACKGROUND OF THE INVENTION

Research has found that the of the application of blue, ultra-violet or a combination of blue and ultra-violet light to a surface is an effective means for reducing the activity of virus and bacteria. Such research, referred to, herein, as Fluorescent Enhancement Theragnosis (FET) technology, has proved itself to provide benefit to practitioners, such as dentist, doctors and surgeons, etc.) in identifying bacteria that would not normally be viewable by the practitioner.

For example, FET has been found use in dental practice to apply light (e.g., blue and/or ultra-violet light) to a patient's mouth to identify virus and/or bacteria and reduce the activity of virus/bacteria and, hence, reduce the likelihood of the patient contracting an infection from the virus and bacteria that are known to exist in the patient's mouth.

Similarly, FET technology provides a doctor or surgeon the ability to view virus and/or bacteria on or within patient and initiate appropriate remedial actions when necessary.

However, the light utilized in FET technology may be harmful to the human eye and, thus, eye protection is required for both the patient and the practitioner to avoid either party from inadvertently viewing the harmful light.

Hence, there is a need in the industry for applying a light therapy to a patient while preventing inadvertent viewing of the applied light.

SUMMARY OF THE INVENTION

Disclosed are devices suitable for the examination, diagnosis and treatment of medical and/or dental conditions, through the application of light from lighting sources to a patient to observe, identify and initiate remedial action to reduce any observed virus and/or bacteria.

Disclosed are devices suitable for the examination, diagnosis and treatment of medical and/or dental conditions through the controlled application of FET lighting technology to a patient.

Disclosed are devices suitable for the examination, diagnosis and treatment of medical and/or dental conditions utilizing a controlled timed application of FET technology to a patient in a manner to avoid the inadvertent exposure of the patient's eyes to the light.

In accordance with the principles of the invention, a plurality of examination/diagnosis devices are disclosed which comprise a plurality of lighting sources (e.g., light emitting diodes (LEDs)) suitable for generating at least one light in at least one wavelength range that is suitable for the identification and diagnosis of medical/dental conditions and for the treatment and monitoring of the effectiveness of said treatment, while preventing inadvertent viewing by a practitioner and/or patient of light that may be harmful if viewed.

BRIEF DESCRIPTION OF DRAWINGS

For a better understanding of exemplary embodiments and to show how the same may be carried into effect, reference is made to the accompanying drawings. It is stressed that the particulars shown are by way of example only and for purposes of illustrative discussion of the preferred embodiments of the present disclosure and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

It is to be understood that the figures and descriptions of the present invention described herein have been simplified to illustrate the elements that are relevant for a clear understanding of the present invention, while eliminating for purposes of clarity, many other elements. However, because these omitted elements are well-known in the art, and because they do not facilitate a better understanding of the present invention, a discussion of such elements is not provided herein. The disclosure herein is directed also to variations and modifications known to those skilled in the art.

DETAILED DESCRIPTION

Figure 1:
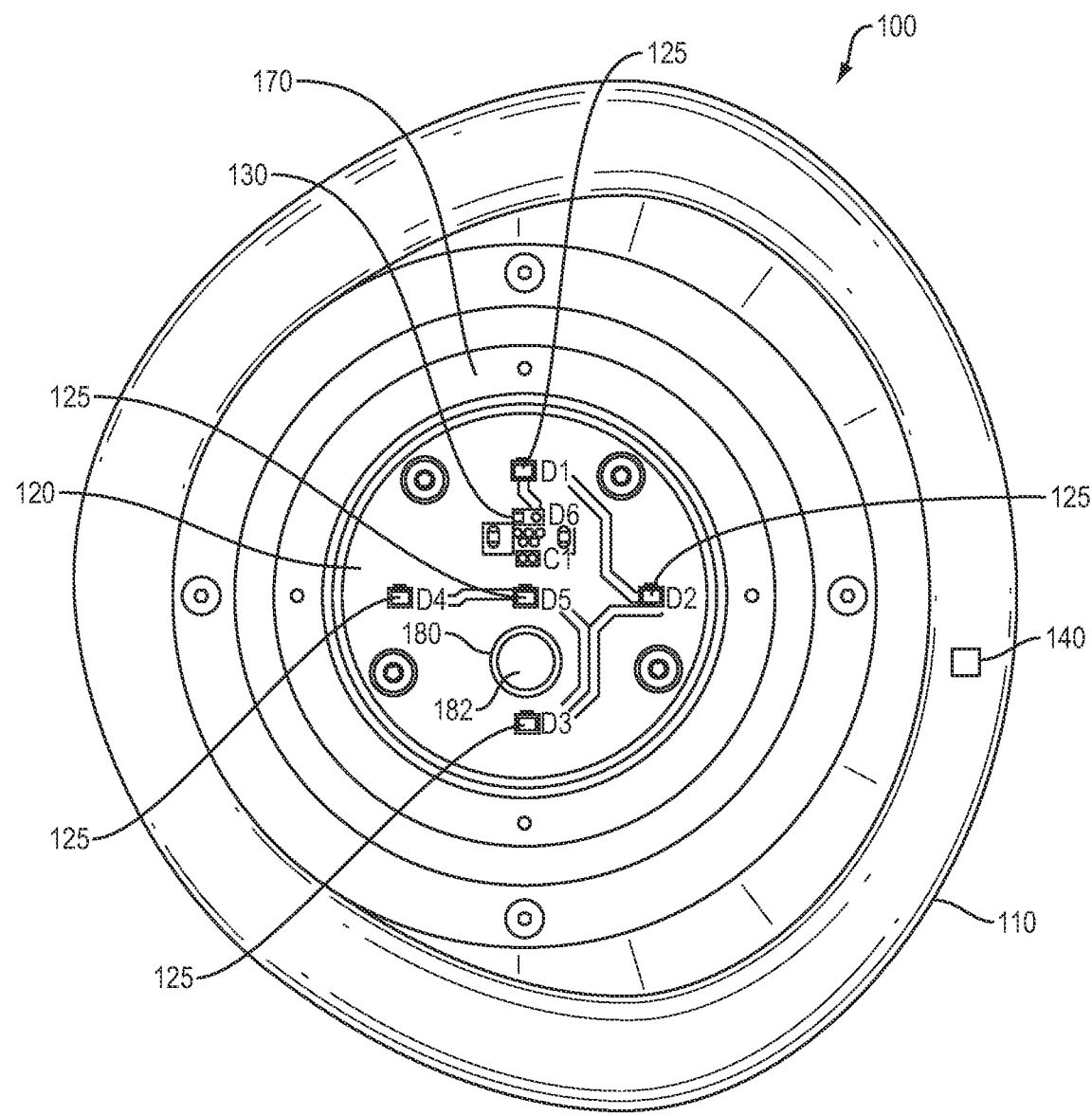
FIG. 1 illustrates a front view of a first exemplary embodiment of an FET based device in accordance with the principles of the invention.

FIG. 1 illustrates a front view of an exemplary embodiment of a diagnosis/treatment device 100 in accordance with the principles of the invention.

In this exemplary embodiment, diagnosis/treatment device 100 comprises a flexible cup element 110 suitable for engaging a surface surrounding a cavity of a patient. The flexible cup element 110, consisting of a medical acceptable material, for example, silicon, which is removably attachable to housing 170. Housing 170 comprises a printed circuit board 120 comprising a plurality of lighting segment 125 wherein lighting segments 125 output a light, and an electronic circuit 130 configured to control an application of a voltage to lighting segments 125.

In accordance with the principles of the invention, the light emitted by lighting segments 125 may be in one or more known wavelength ranges; some of which may be harmful to a practitioner or a patient For example, the light generated by lighting segments 125 may be in one of an ultra-violet light wavelength range that is composed of one or more light wavelength ranges associated with UV-A (i.e., 320-400 nanometers (nm)), UV-B (290-320 nm) and UV-C (220-290 nm). Additionally, lighting segments 125 may generate or emit an ultra-violet light composed of wavelengths from 90-220 nm (i.e., Near UV). Similarly, the light generated or emitted by lighting segments 125 may be in a blue wavelength range that extends from the upper limit of the UV wavelength range (e.g., approximately 400 nm) to the generally accepted "blue" wavelength range (i.e., 450-495 nm). In this case, the term "blue light wavelength range" would further include the violet wavelength range of (i.e., 380-450 nanometers (nm)).

UV and blue light wavelength ranges are known to be harmful to the eye.

In addition, lighting segments 125 may generate light in a one or more light wavelength ranges such as 500-700 nm.

In accordance with the principles of the invention, the lighting segments 125 disclosed, herein, may be selected to generate light in at least one of a non-visible light wavelength range (e.g., UV, near IR and IR) and in a visible light wavelength range (e.g., blue, green, yellow, etc.) and appropriate protections need be established to prevent harmful light radiation from being viewed by the practitioner or the patient.

In one aspect of the invention, lighting segments 125 may include a filter element (hereinafter referred to as excitation filter) (not shown) that is configured to limit a wavelength range of the light emitted by selected ones of lighting segments 125 to a desired wavelength range. For example, LED 125 may comprise at least one light generation element (i.e., a semiconductor die) that emits light in a wavelength range of 380-440 nm, and a corresponding excitation filter may be selected to limit the wavelength range of the light generation element to be less than 425 nm (i.e., a low pass filter). Alternatively, the corresponding excitation filter may be selected to limit the wavelength range of the selected light generation elements to emit light in a wavelength range of 415-425 nm (i.e., nominal value 420 nm). Excitation filters may be selectively applied to the other illustrated lighting segments 125 based on the light generation characteristics of the associated light generation element.

Further illustrated is sensor 140 incorporated into flexible cup element 110. Sensor 140 is configured to provide an indication to electronic circuit 130 that device 100 is appropriately positioned about the surface surrounding a patient's body or body cavity (e.g., mouth, a wound, etc.).

In one aspect of the invention, sensor 140 may be a pressure or contact switch that provides an indication of the sensor is activated by its contact with a surface. In another aspect of the invention, sensor 140 may be an IR (infra-red) sensor that detects reflection of a transmitted signal to determine a distance to a surface and provide an indication the sensor is activated when the determined distance is substantially zero. In another aspect of the invention, sensor 140 may be a proximity sensor that detects the proximity of the sensor to the surface and provides an indication the sensor is activated when the determined proximity to surface is zero or near zero. In another aspect of the invention, sensor 140 may be a heat-activated sensor that measures a temperature. For example, a heat sensor may comprise an infra-red sensor suitable for determining the presence of a heat source. In this case, when sensor 140, in the form of a heat measuring infra-red sensor, is placed close to, or in contact with, a patient, the body temperature of the patient may be measured by the infra-red sensor, and an indication of the placement of sensor 140 proximate to the patient may be transmitted to the electronic circuit 130.

In one aspect of the invention, the indication provided to the electronic circuit 130 may represent a steady voltage level during a period between an initial contact (or determination of proximity) of the sensor with the patient or a surface of the patient to a loss of contact (or determination of proximity) of the sensor with the patient. In another aspect of the invention, the indication provided to the electronic circuit 130 may represent a "one shot" (i.e., at least one pulse) indicating an initial contact (or determination of proximity) of the sensor with the patient and a second "one shot" (i.e., at least one pulse) indicating a loss of contact (or determination of proximity) of the sensor with the patient.

Electronic circuit 130 in response to the indication of the appropriate positioning of (i.e., proximity to, or in contact with, a patient) device 100 may initiate a timer (not shown) and concurrently allow a voltage, through a switch (not shown), to be applied to selected ones of the plurality of lighting segments 125.

In one aspect of the invention the plurality of lighting segments 125 may output a light having a substantially same wavelength (e.g., 420 nm, 640 nm) in at least one light wavelength range. In another aspect of the invention the plurality of lighting segments 125 may output a light at a plurality of different wavelengths (e.g., 420 nm and 460 nm; 420 nm and 650 nm; 600 nm and 650 nm, etc.).

In accordance with the principles of the invention, the output light intensity of the different wavelengths may be the same or may be different. For example, with a known exemplary configuration, wherein a light, e.g., at 420 nm and a light at, e.g., 460 nm is outputted, the intensity of the light emitted at 460 nm may be the same as the light intensity of the light emitted at 420 nm or may be different (e.g., less than) the light intensity of the light emitted at approximately 420 nm.

In accordance with the principles of the invention, the light of different wavelengths may be outputted concurrently or sequentially for a same amount of time or for different times. For example, and using an exemplary example of the output of 420 nm and 460 nm discussed above, the light at 420 nm may be outputted for a first time period and the light at 460 nm may be outputted for a second time period; the first and second time periods being the same or being different. In addition, the first time period and the second time period may be initiated at a same time or at different times so that the emitted lights may overlap in time. Alternatively, the first time period and the second time period may be selected such that the emitted light may be turned off at a same time. Alternatively, the second time period may not be initiated until the first time period has expired (i.e., disjoint light output). In addition, the light outputted by lighting segments 125 may be sequenced to alternate the light output such that the light of a first LED 125 may be turned on/off periodically, while the light of a second LED 125 may be turned on during the off periods of the first LED.

In accordance with the principles of the invention, the light output sequence may generally be one of: concurrent, overlapping or disjointed (i.e., non-overlapping).

Although five (5) lighting segments 125 (designated as D1-D5) are shown, it would be recognized that the number of lighting segments 125 and/or the wavelengths of the light that each of the lighting segments 125 outputs may be altered without altering the scope of the invention.

Further illustrated is image collection or viewing port 180 extending through PCB 120. Image collection or viewing port 180 allows for the insertion of an image viewing/capture device (i.e., a fiber optic cable, a camera, a camera lens, etc.) that allows for the viewing and/or recording of images of the area contained within device 100.

In addition, images viewed through an image viewing/capture device (not shown) may be transmitted to a display screen or a monitoring device for viewing and further submitted to a recording device for the subsequent recording of the images viewed. In one aspect of the invention, the image viewing/capture device (not shown) may include a camera attachment that allows for the capturing and recording of images within the area of the device 100.

In another aspect of the invention, an image capturing device (e.g., a camera) may be inserted through port 180 to enable the practitioner to capture images of the area contained within device 100. The captured images may be projected onto a display screen or monitoring system for viewing and recording.

In one aspect of the embodiment, a lens may be removably attachable to an end of an inserted fiber optic cable, inserted camera or other similar viewing device, to allow for different levels of magnification of the subject area being viewed.

In another aspect of the invention, a filter (referred to as emission filter) may be incorporated onto an end of the image viewing/capture device, wherein the filter limits the wavelength range of the subject area being viewed or of the images of the subject area collected. In a preferred embodiment of the invention, the selection of the filter characteristics of the filter may be based, in part, on the light emitted (i.e., excitation light) by lighting segments 125 and the expected response (emission or fluorescent light) to the excitation light emitted by lighting segments 125.

For example, light emitted at a wavelength of 430 nm may cause bacteria illuminated by the emitted excitation light to emit light (i.e., a fluorescent light) at a wavelength of 600 mn. The filter placed on the end of the image viewing/capture device may block (or attenuate) light below, for example, 440 nm while allowing light of a wavelength greater than 400 nm to pass substantially unattenuated. Similarly, the filter may possess filter characteristics that allow only light within a wavelength range, in this example, of 570-620 to pass.

Further illustrated is flexible membrane 182 spanning image collection opening 180. Membrane 182 provides for a moisture-proof seal to limit and/or prevent exposure by the practitioner of any fluids that may be present within the confines of the examination device. In an alternative embodiment, membrane 182 may be replaced by a conventional "O-ring," which provides a seal around image collection opening 180.

Figure 2:
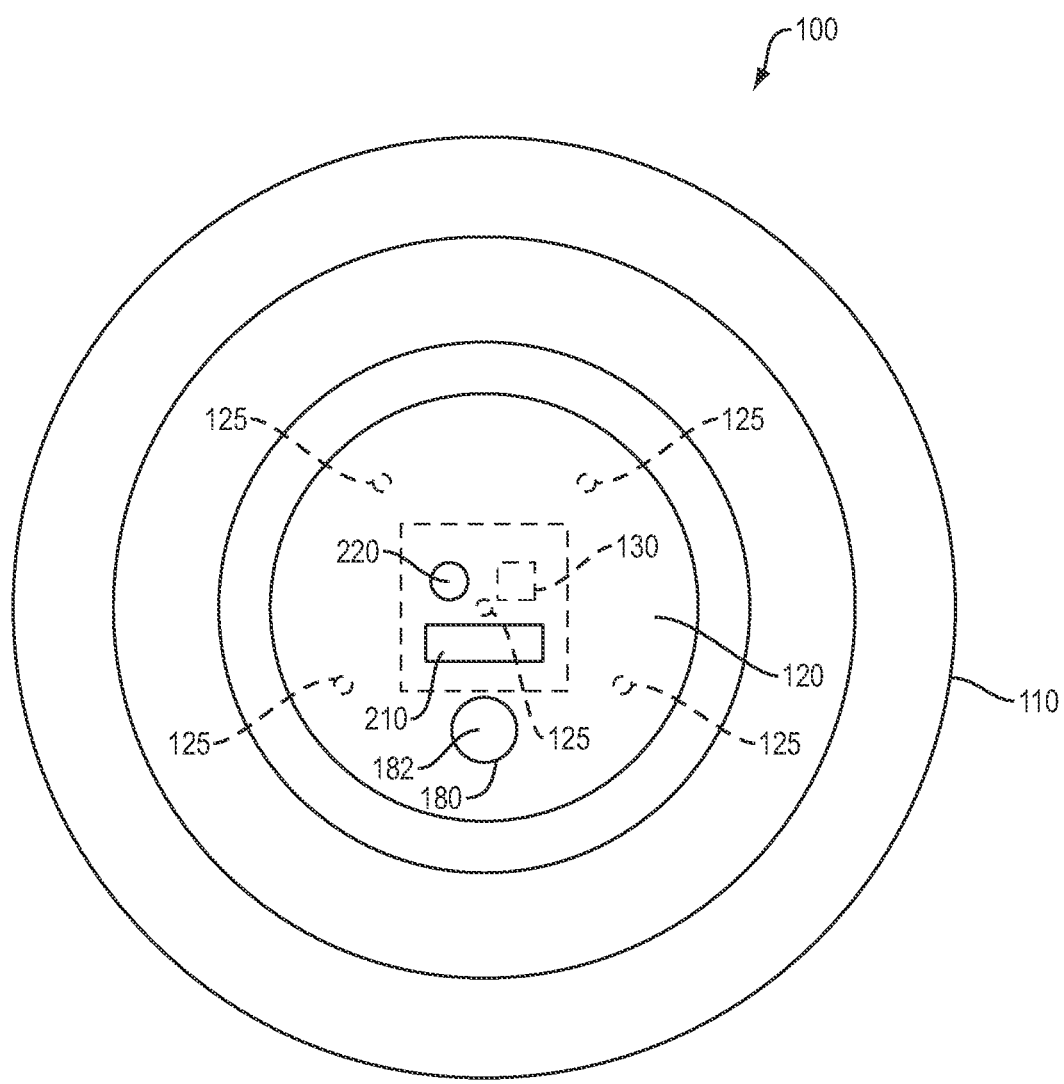
FIG. 2 illustrates a rear view of the exemplary embodiment of the FET device shown in FIG. 1.

FIG. 2 illustrates a rear view of the exemplary embodiment of the device 100 shown in FIG. 1.

In this illustrated embodiment, printed circuit board (PCB) 120 is illustrated within flexible mouth guard element 110, wherein lighting segments 125 and electronic circuit 130 are shown in dotted line as these elements are positioned on a front surface of PCB 120.

Further illustrated is rear facing safety light 220 that provides a light output indicating a voltage has been applied to lighting segments 125. For example, the light output or emitted by safety light 220 may be, for example, one of a red, a green, or a blue color.

In one aspect of the invention, safety light 220 may project a green light when a voltage is applied to lighting segments 125 (i.e., when sensor 140 is active) and projects a red light when the timer is active and sensor 140 is not active (i.e., voltage is removed from lighting segments 125).

Safety light 220 may further represent a switch (e.g., a lighted switch), which when depressed resets the timer within electronic circuit 130. In this case, safety light 220 may project a white light, for example, to indicate device 100 is in a reset condition. For example, the depression of the lighted switch representing safety light 220 may reset a flag that indicates the timer is not active while resetting the timer.

Although a reset switch has been discussed with regard to safety light 220, it would be recognized that safety light 220 may represent a one or more light emitting diodes suitable for generating different wavelengths (e.g., green, red, white) and a separate reset switch (not shown) may be incorporated onto PCB 120 without altering the scope of the invention. Similarly, the reset switch (whether a separate switch or incorporated into safety light 220) may further represent an ON/OFF switch to control the application of a voltage to electronic circuit 130, which controls the application of a voltage to lighting segments 125, as previously discussed.

In accordance with another aspect of the invention, the safety light 220 may represent a light filter that allows for the passage of light having wavelengths that are non-harmful to the eye. In accordance with the principles of the invention, the light (whether blue and/or UV) generated by lighting segments 125 may be blocked by safety light 220 by blocking wavelengths that may be harmful to the user. The illumination caused by the generation of light as seen through light filter of safety light 220 provides an indication of light of lighting segments 125 being generated.

Further illustrated is power source 210 that provides a voltage to electronic circuit 130. Power source 210 may represent a constant direct current voltage source. For example, power source 210 may be a commercially available battery, such as alkaline or rechargeable battery. In another aspect of the invention, power source 210 may represent an input from a remote power source. For example, power source 210 may represent a USB (universal serial bus) connector that may supply a DC voltage, provided by a remote A/C to D/C converter. The USB port may further be used to provide power to recharge a rechargeable battery that may be used to provide a voltage to electronic circuit 130.

As would be appreciated, the voltage may be provided by a power source wired to the electronic circuit that generates a DC voltage or a battery attached to the mouth guard.

Figure 3:
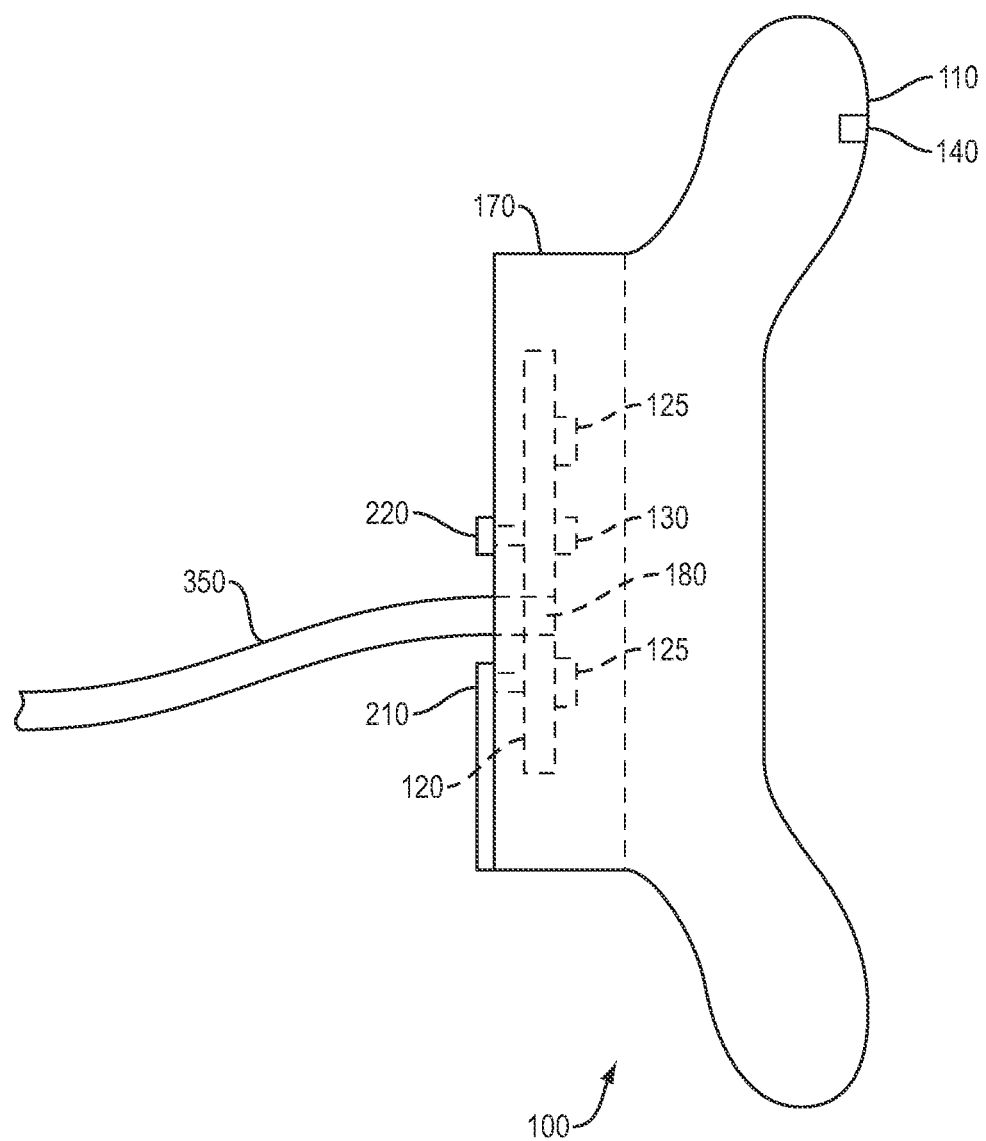
FIG. 3 illustrates a side view of the exemplary embodiment of the FET device shown in FIG. 1.

FIG. 3 illustrates a side view of the exemplary embodiment of a device 100 in accordance with the principles of the invention.

In this illustrated embodiment, device 100 comprises flexible membrane 110, which is shaped to provide 360-degree coverage of an area of a patient. For example, flexible membrane 110 may be centered about a patient's mouth when device 100 is used in dental procedures. Further illustrated is sensor 140 positioned along a leading edge of flexible element 110. Sensor 140 determines a positioning of device 100 with respect to a patient and provides an indication of the proper positioning of device 100 before enabling light from lighting segments 125 to be emitted.

Although a single sensor 140 is shown, it would be recognized that multiple sensors 140 may be incorporated into flexible membrane 110, without altering the scope of the invention.

Flexible membrane 110 may be removably attached to housing 170 to allow flexible membrane 110 to be detached from housing 170. Within housing 170 is shown PCB 120 including electronic circuit 130 and lighting segments 125. Further illustrated are safety light 220 and battery or DC power source 210 in contact with PCB 120 and electronic circuit 130.

In one aspect of the invention flexible membrane 110 may be removably attached to housing 170 to allow for deep clearing or sterilization of flexible membrane 110 or for the interchangeability of flexible members 110 of different shapes to accommodate different body cavities or wounds.

In one aspect of the invention, fiber optic cable 350 may comprise a plurality of individual fiber optic cables, some of which may comprise a camera, a lens or a filter, or a combination, thereof, that allows for capturing of images, while others may allow for the direct viewing of the area.

For example, a filter, referred to as an emission filter, may be incorporated onto one end of fiber optic cable 350 to limit wavelengths viewable (or captured) through fiber optic cable 350.

In accordance with another aspect of the invention, a miniature video recording device or camera (not shown) may be directly attached to device 100 to allow for the capturing of images within device 100 through viewing port 180. The video recording device or image collection device (e.g., a camera) in communication with fiber optic cable 350 to transfer collected images to, for example, a monitoring or a recording device (not shown).

In another of the invention, the image capturing device may include a wireless transmitter that is capable of transmitting images collected or viewed directly to, for example, a monitoring or receiving device (e.g., a television, a computer monitor and/or a recording device). The wireless transmitter may utilize one of a near-field communication, a BLUETOOTH communication, or similar communication protocols. In still another aspect, the wireless device may be connected to a local area network (LAN) that allows for the distribution of images collected to be displayed on a monitoring device.

Figure 4:
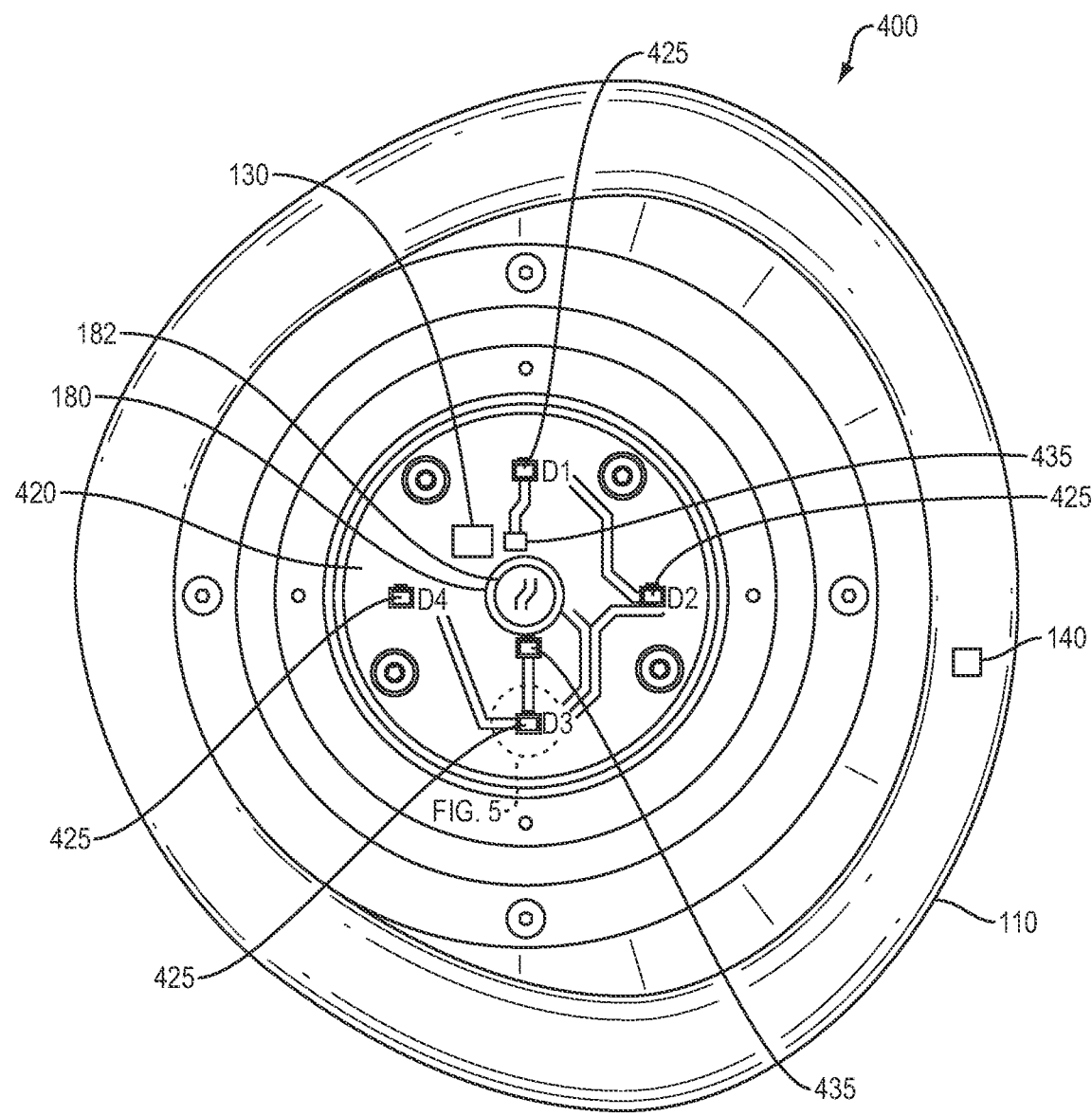
FIG. 4 illustrates a front view of a second exemplary embodiment of the FET device shown in FIG. 1.

FIG. 4 illustrates a front view of a second exemplary embodiment of a diagnosis/treatment device in accordance with the principles of the invention.

In this second exemplary embodiment, diagnosis/treatment device 400 comprises flexible membrane 110 including contact/proximity switch 140, PCB 420 and electronic circuit 130, which are similar to those elements disclosed with regard to FIG. 1.

Further illustrated is a plurality of lighting sources (hereinafter referred to as LEDs) 425 configured to output light in a plurality of desired wavelength ranges.

In this illustrated exemplary second embodiment, PCB 420 includes LEDs 425 and LEDs 435, wherein LEDs 435 may comprise lighting segments that emit a white light and LEDs 425 may emit light in one or more wavelength ranges (e.g., ultra-violet, visible, infra-red).

The use of LEDs 435 provides for the illumination of the area or cavity covered by diagnosis/treatment device 400. While LEDs 435 are shown and discussed, it would be recognized that LEDs 435 are merely optional elements and need not be included with device 400 without altering the scope of the invention claimed.

LEDs 425, similar to lighting segments 125, are arranged on printed circuit board 420 to provide a substantially uniform distribution of light emitted by selected ones of LEDs 425. LEDs 425 may output or emit a light at a plurality of different wavelengths (e.g., 420 nanometers (nm) and 460 nm; 420 nm and 650 nm, 600 nm and 650 nm, etc.), to allow for different configurations of light therapy to be provided to a patient.

Further illustrated is viewing port 180 positioned, in this case, substantially centered within PCB 420. Viewing Port 180 allows for the insertion of an image viewing device (e.g., a fiber optic cable 350 or camera (not shown)) that allows for the viewing by the practitioner of the area contained within device 400 and/or image capture and collection.

The images viewed through the fiber optic cable 350 may further be transmitted to a display screen or a monitoring device for the viewing and subsequent recording of the images seen through the inserted fiber optic cable. In one aspect of the invention, the fiber optic cable 350 may include a camera attachment that allows for the capturing and recording of images within the area of the device 400.

In another aspect of the invention, an image capturing device (e.g., a camera) may be inserted through port 180 to enable the practitioner to capture images of the area contained within device 400. The captured images may be projected onto a display screen or monitoring system for viewing and recording.

In one aspect of the embodiment, a lens may be removably attached to the end of the cable 350, camera, other viewing device to allow for different lens of magnification of the subject area being viewed.

In another aspect of the invention, a filter may be incorporated onto an end of the fiber optic cable 350 (or a camera), wherein the filter limits the wavelength range of the subject area being viewed or of the images of the subject area collected. In a preferred embodiment of the invention, the selection of the filter characteristics of the emission filter may be based, in part, on the light emitted (i.e., excitation light) by LEDs 425 and the expected response (fluorescent light) to the emitted excitation light.

Further illustrated is flexible membrane 182 spanning viewing port opening 180. Membrane 182 provides for a moisture-proof seal to limit and/or prevent exposure by the practitioner of any fluids that may be present within the confines of the device 400.

Figure 5:
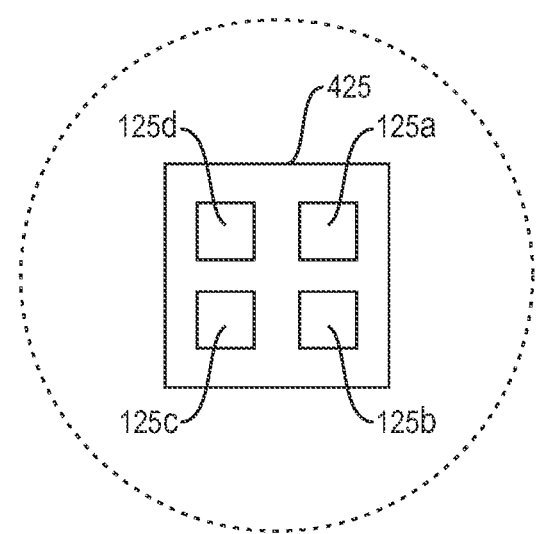
FIG. 5 illustrates an expanded view of the area referred to in FIG. 4.

FIG. 5 illustrates an expanded view of the area designed A in FIG. 4, showing LED 425. In this illustrated embodiment of LED 425, LED 425 is composed of a plurality of lighting segments 125 (referred to as 125A, 125B, 125C and 125D), each of which is similar to lighting segment 125 discussed with regard to FIG. 1 and generates light within a desired wavelength range. For example, LED 125A may represent a light source emitting light in a 420 nm wavelength range, LED 125B may represent a light source emitting light in a 460 nm wavelength range, LED 125C may represent a light source emitting light in a 530 nm wavelength range and LED 125D may represent a light source emitting light in a 635 nm wavelength range.

While LED 425 is represented by four (4) lighting segments 125 (designated D1-D4), it would be recognized that the number of lighting segments 125 incorporated into LED 425 may be increased or decreased without altering the scope of the invention claimed. In addition, while exemplary wavelength ranges or values for each of the illustrated lighting segments 125 is disclosed, it would be recognized that the wavelength ranges or values disclosed are merely representative values and lighting segments 125A-125D may emit light in other wavelengths ranges, which are considered within the scope of the invention claimed.

Figure 6:
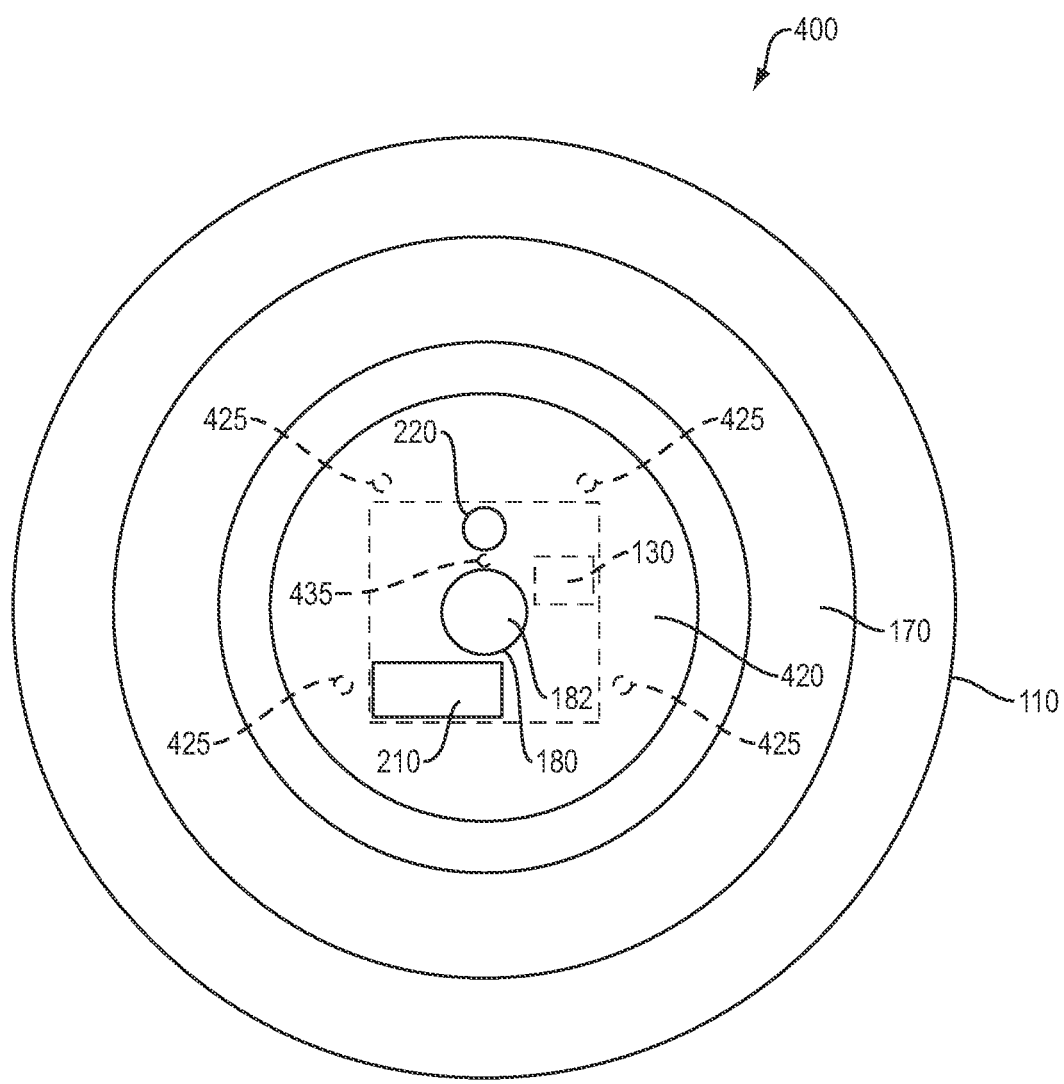
FIG. 6 illustrates a rear view of the second exemplary embodiment of the FET device shown in FIG. 4.

FIG. 6 illustrates a rear view of the second exemplary embodiment of the device shown in FIG. 4.

Similar to the exemplary embodiment shown in FIG. 2, device 400 includes power supply 210, safety light 220 and image viewing device port 180 including membrane 182. Electronic circuitry 130 controls the passage of voltage from power supply 210 to one or more of the lighting segments 125A-125D in each of LEDs 425. Safety light 220, indicates the status of the light emitted by one or more of LEDs 425.

Although not shown, it would be recognized that device 400 may possess a profile, in side-view, similar to the side-view of device 100 shown in FIG. 3, so that the flexible membrane 110 may substantially surround an area to which light therapy is to be applied.

Figure 7:
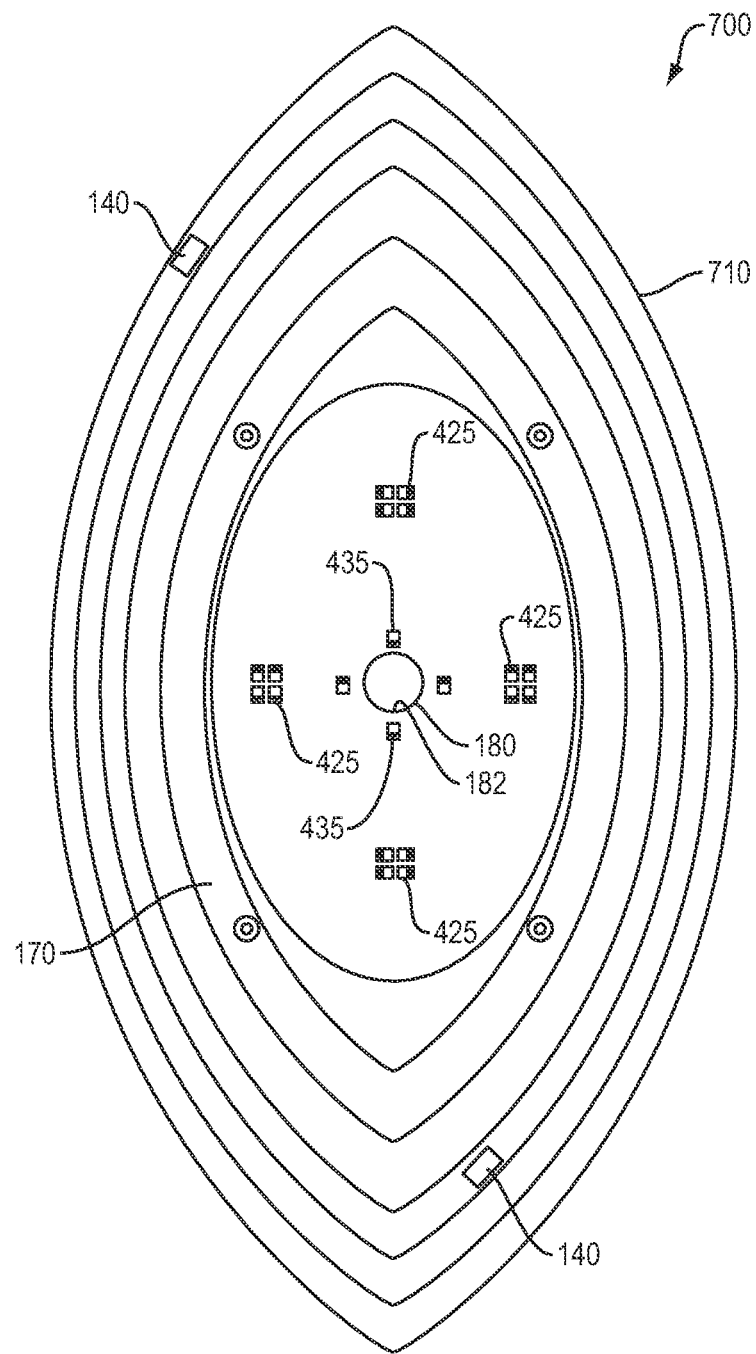
FIG. 7 illustrates a second aspect of the second exemplary embodiment of an FET device shown in FIG. 4.

FIG. 7 illustrates a second aspect of the second exemplary embodiment of diagnosis/treatment device 700 in accordance with the principles of the invention.

In this illustrated second aspect, device 700 comprises PCB 720 comprising a plurality of LEDs 425 and port 180 with membrane 182, as previously discussed. Further illustrated is flexible membrane 710 including at least one proximity/contact switch 140, as previously discussed.

As shown PCB 720 and flexible membrane 710, which are comparable to PCB 120 and flexible membrane 110, are constructed in an oval or elongated shape to properly cover the area to be examined. Device 700 may be suitable for application, for example, for an OB-GYN (obstetrician-gynecologist) practitioner.

Device 700, similar to devices 100 and 400 operates to emit light of one or more wavelengths and is shaped to enable the practitioner to provide treatment to a medical conditions arising in the gynecological medical field, for example.

Although not shown, it would be recognized that device 700 has a profile, in side-view, similar to the side-view of device 100 shown in FIG. 3, wherein sensor 140, within flexible membrane 110 provides an indication of the proper position of device 700 prior to initiating light therapy.

Figure 8:
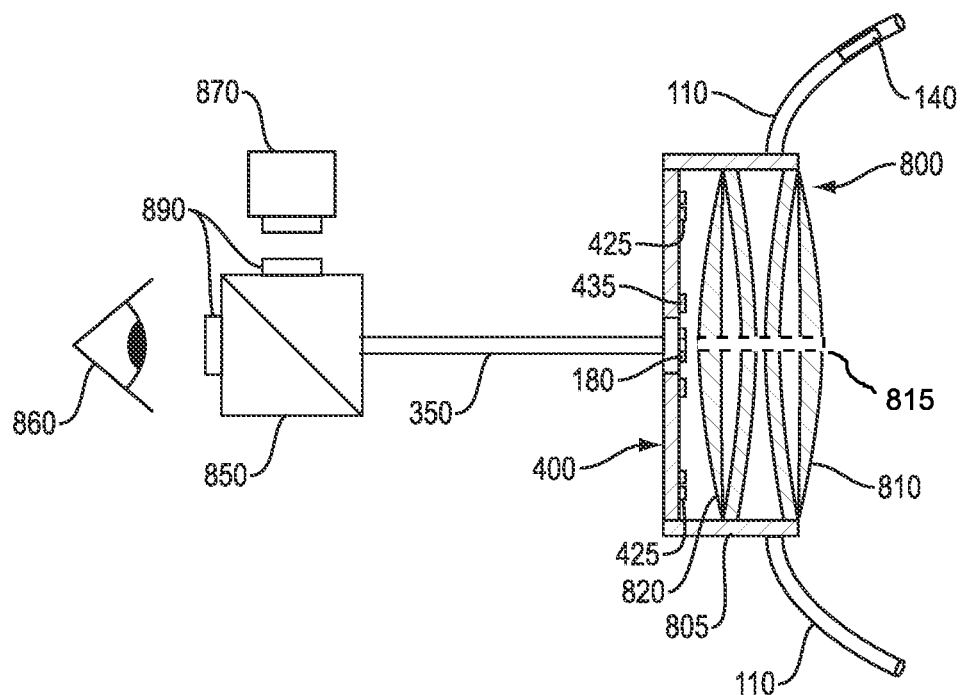
FIG. 8 illustrates a side view of a third aspect of the second exemplary embodiment of the FET device shown in FIG. 4.

FIG. 8 illustrates a side view of an exemplary application of the exemplary embodiments of a diagnosis/treatment device disclosed, herein.

In this illustrated aspect, which is applicable to a dermatological field of medicine, for example, diagnosis/treatment device 800 comprises diagnosis/treatment device 400, including PCB 420 containing LEDs 425 and port 180, and flexible membrane 110, as previously described.

Flexible membrane 110 includes switch 140, which, as previously described, provides an indication to electronic circuitry 130 on PCB 420 to provide control of an application of light from one or more of lighting segments 125A-125D within LEDs 425.

Further illustrated is lens system 805, which in this illustrated example, comprises objective lens 810, 820 that focuses the light emitted by one or more of LEDs 425.

Although two lens 810, 820 are shown it would be appreciated that the number of lens within lens system 805 may be increased, or deceased, without altering the scope of the invention claimed.

Further illustrated is image capturing device, represented as fiber optic cable 350, extending from device 400 and providing images captured within the area contained within flexible membrane 110. Although a fiber optic cable is illustrated, it would be recognized, and as previously discussed, the image capture device may comprise a camera (not shown) inserted into, or inserted through, viewing port 180. Images captured by the not shown camera may be provided through fiber optic cable 350, or wirelessly, to a monitoring device, for example.

In this illustrated case images viewed by cable 350 may be provided to the illustrated optical splitter 850 that directs the images viewed, in this illustrated case to a practitioner's eye 860 and provided to a second device 870. The illustrated second device 870 may be one of a monitoring device (e.g., a television display, a computer monitor display) and/or a recording device.

Although, FIG. 8 illustrates an optical splitter 850 that allows for the concurrent direct viewing and image capturing of images provided through fiber optic cable 350, it would be recognized that fiber optic cable 350 may be applied directly to a display (e.g., television) or a monitoring system, wherein the viewed area may be viewed by others. In addition, the images may be recorded on a medium (e.g., optical disk, solid state memory, etc.) for later review and evaluation.

Further illustrated are filters 890 (referred to as emission filters), which limit the light wavelength range viewed by the practitioner 850 and captured by device 870. Filters 890, similar to the filter positioned on the end of fiber optic cable 350, disclosed previously, are configured to block, in whole or in part, light emitted by LEDs 425 (i.e., excitation light) while allowing fluorescent light to pass substantially unattenuated.

In accordance with the principles of the invention, the filter characteristics of filters 890 may be selected based on light therapy to be utilized. That is, the filter characteristics of emission filters 890 may be selected based on the selection of the excitation light expected to be emitted by the one or more of lighting segments 125A-125D of the plurality of LEDs 425. Alternatively, the filter characteristics of emission filters 890 may be selected based on the expected wavelength range of the fluorescent light emitted by an object when illustrated by excitation light expected to be emitted by the one or more of lighting segments 125A-125D of the plurality of LEDs 425.

Although emission filters 890 are illustrated as being associated with the illustrated optical splitter 850, it would be recognized that emission filter 890 may be incorporated onto an end of fiber optic cable 350. In addition, when a camera is utilized as an image capture device, then filter 890 may be incorporated onto a lens of utilized camera to limit the wavelength range of the captured images to a desired wavelength range.

In one aspect of the invention, a hole or passthrough may be inserted through lens 810, 820 that is aligned to the optical axis of the illustrated fiber optic cable 350, or the not shown camera, insert into viewing port 180. The hole or passthrough within lens 810, 820 allows for an unobstructed view of area being viewed. In still another aspect of the invention, fiber cable 350 (or not shown camera) may be inserted through hole or passthrough within lens 810, 820. The images captured by cable 350 (or camera) may be applied to splitter 860, for example, as discussed. In still another aspect of the invention, a camera may be installed on a front surface of lens 810 to capture images of an area being viewed. The images captured by the installed camera may be provided to splitter 860, for example, as discussed.

Figure 9:
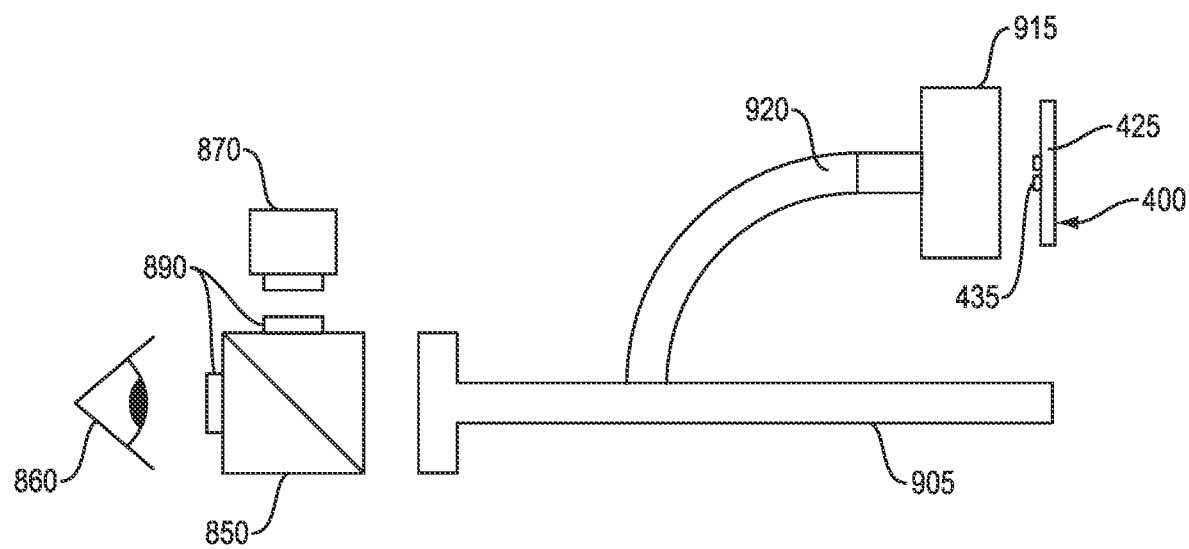
FIG. 9 illustrates a side view of a fourth aspect of the second exemplary embodiment of the FET device shown in FIG. 4.

FIG. 9 illustrates a side view of a second exemplary application of the exemplary embodiment of a diagnosis/treatment device disclosed, herein.

In this illustrated aspect, diagnosis/treatment device 400 comprises PCB 420, including LEDs 425/435 is optically attached to a conventional endoscope 905 through optic fiber 920.

In this exemplary application, PCB 400 is positioned within housing 915, which similar to flexible membrane 110 limits the inadvertent exposure of the practitioner to one or more of the lights emitted by lighting segments 125A-125D of LEDs 425.

In one aspect of the invention, LEDs 435, emitting a white light, as previously discussed, may be used to illuminate a body cavity into which endoscope 905 is placed. Once the endoscope 905 is properly positioned, light emitted by one or more of lighting segments 125A-125D of LEDs 425 may then be applied to provide diagnosis and treatment of the area, as previously discussed In addition, a practitioner 860 may view light reflected from inside the body cavity as is known in the art.

In this illustrated case, an optical splitter 850 may allow for the concurrent direct viewing by the practitioner 860 and an image capture device 870, that may display the captured images on a display screen or monitoring device for viewing and subsequent recording of the captured images.

In another aspect of the invention, device 800 may be incorporated into housing 915. In this aspect of the invention, device 800 operates in a manner as previously discussed, wherein light emitted by one or more of lighting segments 125A-125D within LEDs 425 is presented to endoscope 905 and applied to a patient. Light generated by an object subjected to the excitation light emitted by LEDs 425 is captured and displayed, as previously described. In this aspect of the invention, optical splitter 860 is unnecessary.

In accordance with the principles of the invention, sensor 140 (FIG. 1), which provides an indication of proximity to a patient that controls the initiation of an application of voltage to LEDs 425, may be replaced by a sensor that provides the indication of proximity or contact when proximity or contact is made with housing 915. Alternatively, sensor 140 may be replaced by a switch that may be manually controlled to provide an indication to electronic circuit 130 to initiate an application of voltage to LEDs 425.

Hence, sensor 140, more generally, provides the indication of initiation of the application of a voltage to LEDs 425 (LEDs 435 and/or lighting segments 125) when sensor 140 determines device 100, 400, etc. is appropriately positioned, which may be performed dynamically by the detection of proximity or contact with a patient or an object or manually by a practitioner.

Figure 10:
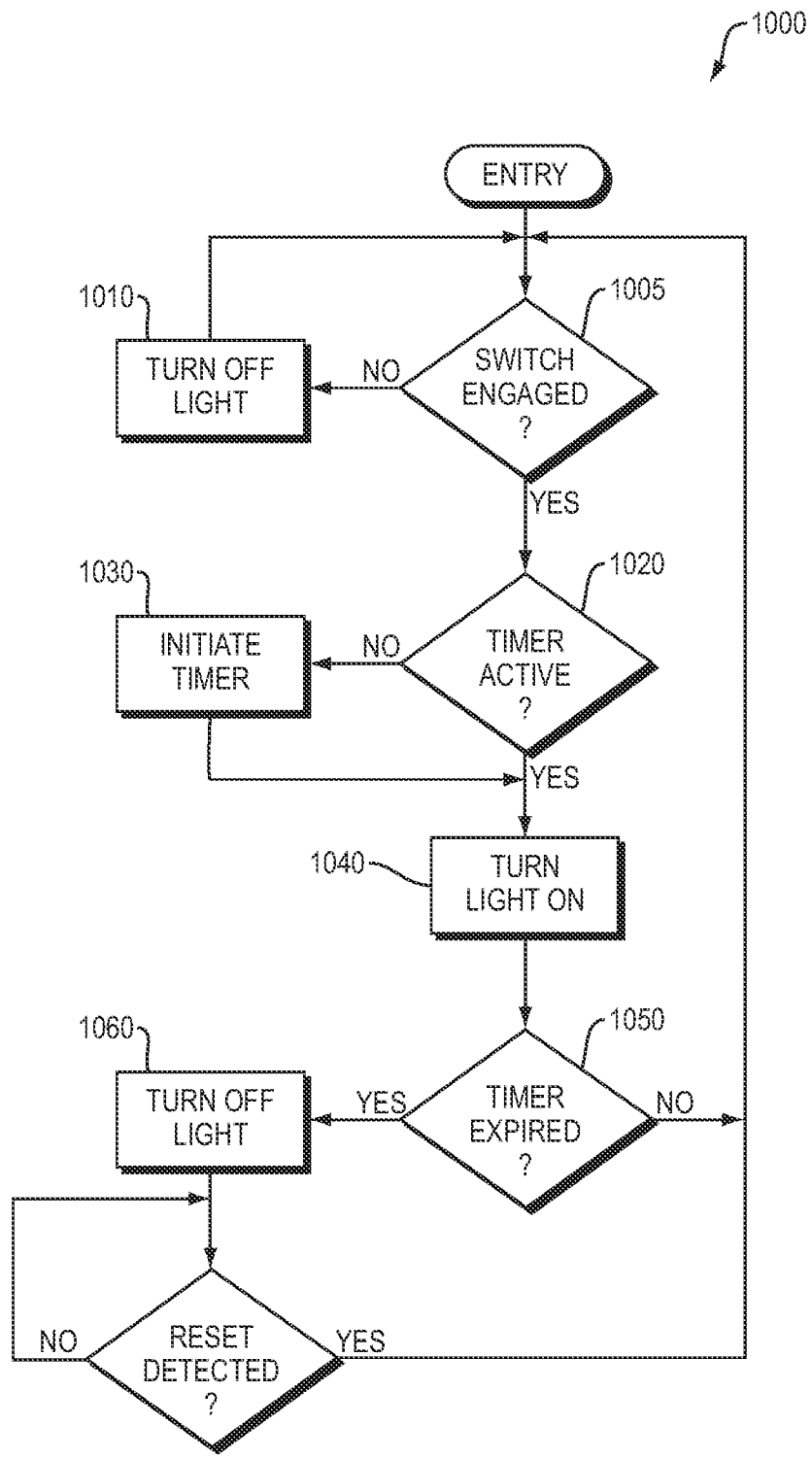
FIG. 10 illustrates a side view of a second aspect of the fifth exemplary embodiment of the FET device shown in FIG. 4.

FIG. 10 illustrates a flow chart of an exemplary process 1000 for safely controlling the application of a light to a patient using one of the devices disclosed, herein.

In accordance with the principles of the invention, a determination is made whether the sensor 140 is in contact with (or proximate to) with a patient. If the answer is negative, then processing proceeds to step 1005, where the voltage is removed from LEDs 425 (i.e., lighting segments 125A-125D).

However, if the answer is in the affirmative, then processing proceeds to step 1020, where a determination is made whether a timer is active. If the timer is not active, then processing proceeds to step 1030, where a countdown timer is initiated (for example, the timer may be initiated for a pre-determined time value, such as 2 minutes). Processing then proceeds to step 1040, where a voltage is applied to lighting segments 125.

Returning to step 1020, if the timer is indicated as being active, processing proceeds to step 1040, where the voltage is applied to selected ones of lighting segments 125A-125D of LEDs 425. As discussed above the application of the voltage to the lighting segments 125A-125D may be such that the output of the light may be one of concurrent, overlapping and disjointed.

Processing proceeds to step 1050 where a determination is made whether the timer has expired (i.e., counted down to zero). If the timer has expired, the processing proceeds to step 1060 where the voltage applied to LEDs 425 is removed. Otherwise, processing proceeds to step 1005 where a determination is made whether the sensor 140 is engaged.

Figure 11:
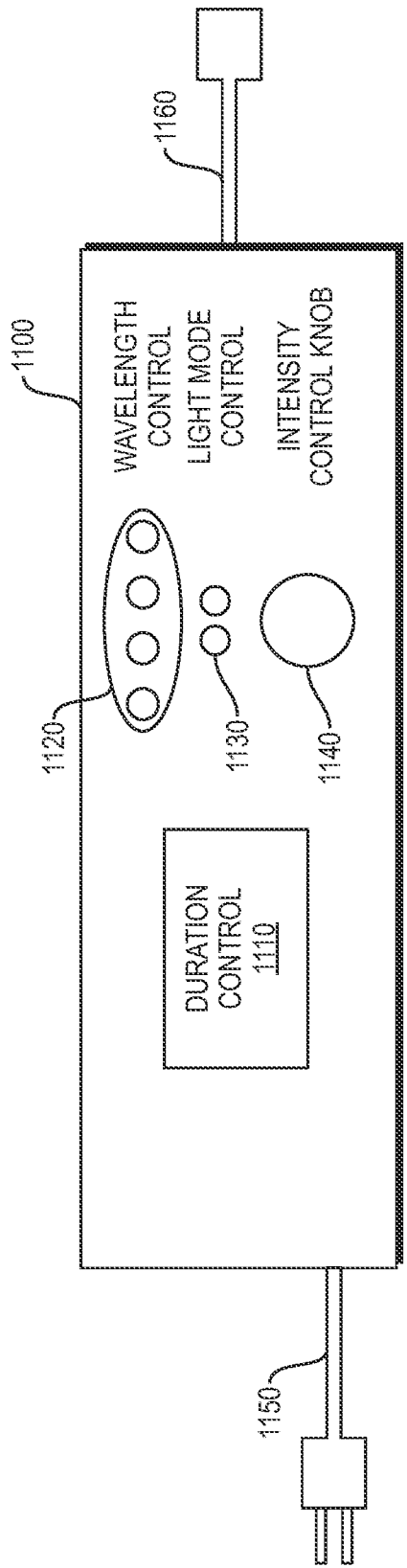
FIG. 11 illustrates an exemplary control device for controlling the application of FET technology by the exemplary embodiments shown, herein.

FIG. 11 illustrates an exemplary control processor in accordance with the principles of the invention.

Control processor 1100 comprises a display 1110, a wavelength control selector 1120, a light mode controller 1130 and a light intensity control 1140. Further illustrated is electrical connector 1150, which may be inserted into an electrical outlet to provide main power (e.g., 120 or 220 volts) to control processor 1100.

Further illustrated is transfer cable 1160 that may be removably attachable to PCB 100/400, etc. Transfer cable 1160 provides a means to supply one or more of a power and instruction to PCB 100/400.

In one aspect of the invention, transfer cable 1160 may provide a voltage to PCB 100/400, which may be applied to electronic circuit 130. The supplied voltage may then be selected applied to LEDs 425.

In another aspect of the invention, transfer cable 1160 may provide instruction to PCB 100/400, wherein the instructions may be interpreted by electronic circuit 130 to control operation of LEDs 425. The provided instructions may, for example, may direct electronic circuit 130 to provide voltage to selected ones of lighting segments 125A-125D of LEDs 425 (or to LED 435, when available), a duration of the applied voltage, a drive current to control an output intensity of the selected ones of lighting segments 125A-125D, etc.

Display 1110 provides information to a practitioner regarding the operation of diagnosis/treatment device 100 (400, etc.). For example, the light outputted, the duration of the outputted light, and may provide instruction regarding the timing of one or more of the lights to be outputted.

Wavelength control 1120, which is illustrated as comprising 4 elements, provides control of the selection of selected ones of the exemplary lighting segments 125A-125D contained within LED 425. Based on the selection of one or more of the elements within wavelength control 1120, the light outputted by LEDs 425 may be adapted for a particular medical/dental procedure.

Light mode control 1130 provides for the operation of the voltage applied to LEDs 425. In one aspect, voltage may be applied to LEDs 425 continuously for a known period of time. In another aspect of the invention, voltage may be applied to LEDs 425 in pulsed manner.

Intensity control knob 1140 controls the intensity of the light outputted by devices 100/400, etc.

Although controller 1100 is shown as providing a practitioner with the ability to manually control the application of a voltage to devices 100/400 etc., in another aspect of the invention, the setting of LEDs, mode and intensity may be preprogrammed into a memory, for example, wherein the preprogramed setting may be determined based on the procedure to be performed.

In this case, the controller 1130 may include an interface, e.g., display 1110, that allows the practitioner to select the specific procedure to be performed, wherein the settings associated with the operation of devices 100/400, etc., (i.e., wavelength, duration, etc.) are accessed and applied to device 100/400, etc.

Although control device 1100 is shown being connected to a main power supply through cable 1150, it would be recognized that device 1100 may be incorporated onto a rear surface of device 100/400, for example, wherein the interface may allow for the manual selection of operational characteristics or may be pre-programed for specific operational characteristics.

Figure 12:
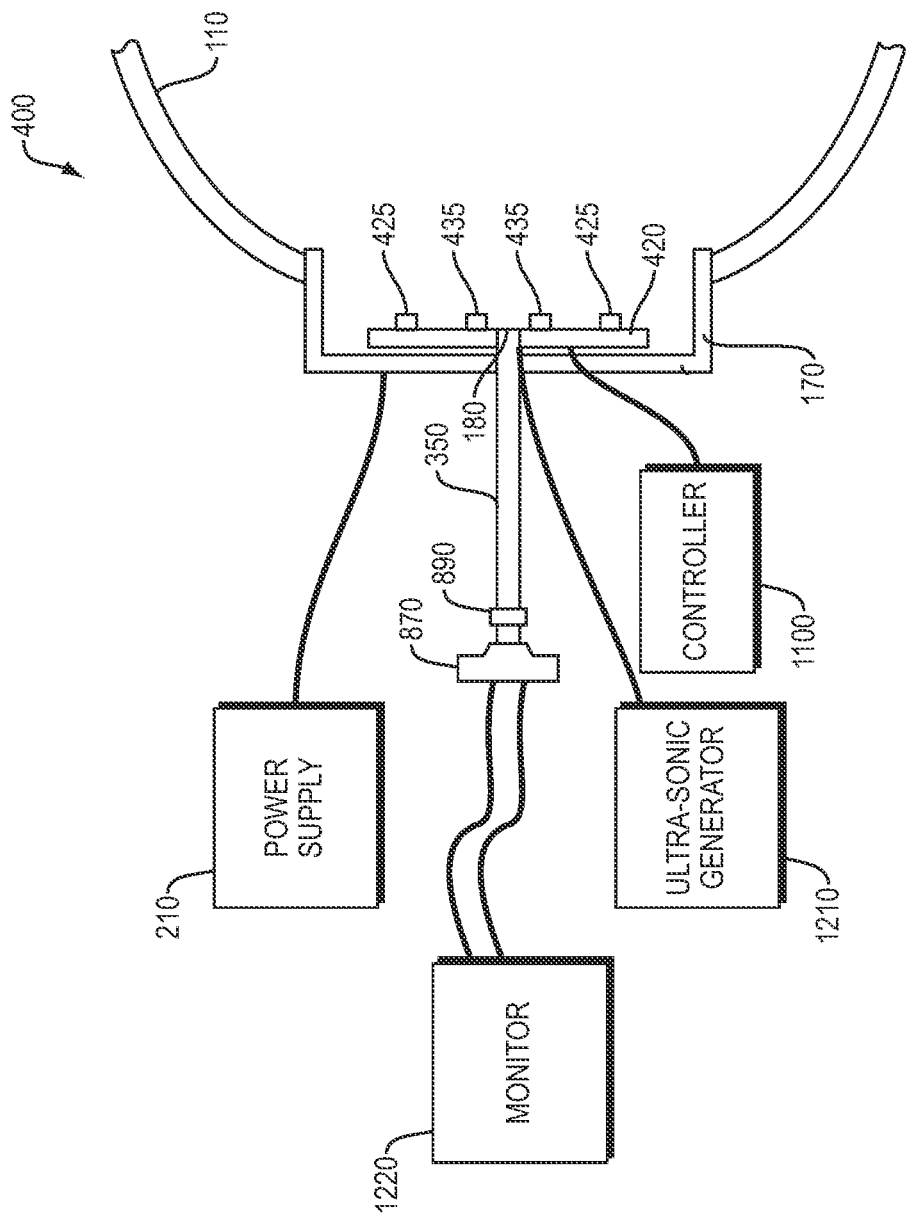
FIG. 12 illustrates an exemplary system for incorporating the diagnosis/treatment device(s) disclosed, herein.

FIG. 12 illustrates an exemplary system for incorporating the diagnosis/treatment device(s) disclosed, herein.

In this exemplary system configuration, diagnosis/treatment device 400 including PCB 420 containing LEDs 425, 435, as previously disclosed, is illustrated. Further illustrated is power supply 210 that provides power to device 400 and controller 1100 that provides control instructions to device 400. Further illustrated is optic fiber cable 350 providing images of the area illuminated by LEDs 425, 435 to camera device 870 which includes filter 890.

Further illustrated is display 1220 connected to camera 870 to display images captured by camera 870. Camera 870 may be connected to display 1220 through a wired or wireless (e.g., BLUETOOTH, NFC) communications.

Further illustrated is ultra-sonic generator 1210, which provides an ultra-sonic signal into device 400. In one aspect of the invention, the ultra-sound generated by generator 1210, may be applied through a separately provided (not shown) cable or may be supplied through the illustrated optical cable 350

In summary, a diagnosis/treatment device is disclosed that allows for the safe application of a light to a patient while limiting the potential of the practitioner inadvertently viewing the light. In accordance with the principles of the invention, a sensor provides an indication that the device is appropriately positioned, where the indication causes a timer to be initiated and further turns on the light emitting diodes, wherein the timer limits the total time the light is turned on. Thus, the lights are turned on only when the device is properly positioned and the timer is active. Once the device is not properly positioned or the timer is no longer active, the lights are turned off by the removal of a voltage to the light emitting diode elements.

Further disclosed is a viewing port that allows for the viewing and/or recording of areas that are experiencing the light therapy disclosed.

Although exemplary wavelengths are disclosed, it would be appreciated that any combination of wavelengths may be selected based on their wavelength range being within known light ranges.

It would be appreciated that various modifications and changes can be made without departing from the scope of the invention as set forth in the claims. Accordingly, the specification is to be regarded in an illustrative manner, rather than with a restrictive view, and all such modifications are intended to be included within the scope of the invention. Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instances, the terms "about" may include numbers that are rounded (or lowered) to the nearest significant figure.

It is expressly intended that all combinations of those elements that perform substantially the same function in substantially the same way to achieve the same results are within the scope of the invention. Substitutions of elements from one described embodiment to another are also fully intended and contemplated

What is claimed is:

1. An endoscopic device to assist in the diagnosis and the treatment of a condition within a body cavity of a patient, said device comprising:
   a tubing element comprising:
      a main section comprising:
         plurality of a plurality of optic fibers and lens; and
         a viewing port on a proximal end of main section of said tubing element, wherein said plurality of optic fibers extend to a distal end of said tubing section, a light adaptor section intersecting said main section, said light adaptor section comprising:
a housing; and
a plurality of said optic fibers extending from said housing through said main section to said distal end of said tubing section, wherein said housing is configured to:
engage a treatment device, said treatment device comprising:
a plurality of lighting sources, said plurality of lighting sources comprising:
at least one lighting segment, wherein said at least lighting segment is configured to:
emit a light in a desired wavelength range toward a proximal end said plurality of optic fibers extending from said housing;
a sensor configured to:
generate an indication of placement of said treatment device within said housing: and
an electronic circuit configured to:
receive said indication; and
control an application of a voltage to said at least one lighting segment in selected ones of said plurality of lighting sources based on said received indication of appropriate positioning of said treatment device.

2. The device of claim 1, wherein said treatment device further comprising:
an image capture device, said image capture device in optical communication with selected ones of said plurality of optical fibers within said light adaptor section.

3. The device of claim 2, wherein said image capture device is one of:
a camera and a CCD device.

4. The device of claim 3, comprising:
an emission filter positioned on an end of said image capture device, said emission filter configured to limit a wavelength range viewable through said emission filter.

5. The device of claim 1, wherein said desired wavelength range is one of:
ultra-violet wavelength range, visible wavelength range and infra-red wavelength range, wherein said visible wavelength range is at least one of: a violet wavelength range, a blue wavelength range, a cyan wavelength range, a green wavelength range, a yellow wavelength range, an orange wavelength range and red wavelength range.

6. The device of claim 1, wherein said sensor comprises one of: a contact sensor, an IR transmitter/detector sensor, a proximity sensor, a heat sensor and a switch.

7. The device of claim 1, wherein said electronic circuit comprises:
a timer, said timer configured to:
provide an indication of an expiration of a time to said electronic circuit, wherein said electronic circuit is configured to:
receive said indication of said expiration of said time; and
remove said application of said voltage to said at least one lighting segment of said selected ones of said plurality of lighting sources in response to said received indication of said expiration of said time.

8. The device of claim 7, wherein said timer is initiated to said time based on said received indication of appropriate positioning.

9. The device of claim 1, comprising:
a controller configured to:
provide instruction to said electronic circuit, wherein said instruction comprising at least one of: an emission of light from selected ones of said lighting segments, a duration of said emission of light from said selected ones of said lighting segments, and a turn on time of said selected ones of said selected lighting segments.

10. The device of claim 9, comprising:
a user interface configured to:
select said instruction, wherein said selection of said instruction is one of: manual and automatic.

11. The device of claim 1, wherein said plurality of lighting sources emit said light in one of: a substantially same wavelength and at different wavelengths.

12. The device of claim 1, wherein said plurality of lighting sources emit light at different light intensities.

13. The device of claim 1, wherein said plurality of lighting sources emit said light as one of: concurrently and sequentially, in one of: continuous and pulsed modes.

14. The device of claim 1, wherein said appropriate position with respect to said patient is one of: contact with said patient and proximity to said patient.

15. The device of claim 1 comprising:
a viewing adaptor section comprising:
an optical splitter in optical communication with said viewing port, said optical splitter configured to:
divide light emitted through said viewing port to a first port and a second port; and
an image capture device in optical communication with said first port.

16. The device of claim 15, comprising:
an emission filter associated with each of said first port and said second port.

17. A body cavity treatment device comprising:
an endoscope comprising:
an endoscopic tube comprising:
a plurality of optical fibers, wherein said selected ones of said plurality of optical fibers are joined together forming optical bundles;
a light adaptor intersecting said endoscopic tube, said light adaptor comprising:
a housing; and
a second plurality of optical fibers extending from said housing through said endoscopic tube adjacent said optical bundles;
a light therapy treatment device configured to:
engage said housing, said light therapy treatment device comprising:
a plurality of lighting sources comprising a plurality of light emitting diodes arranged in optical communication with said second plurality of optical fibers extending from said housing, said plurality of lighting sources configured to emit a light into said second plurality of optical fibers, wherein said housing further comprising a sensor configured to:
generate an indication of placement of said light therapy treatment device within said housing: and
an electronic circuit configured to:
receive said indication; and
control an application of a voltage to said at least one of said plurality of lighting sources based on said received indication of positioning of said light therapy treatment device within said housing.

18. The body cavity treatment device of claim 17, comprising:
a viewing adaptor arranged in optical communication with said endoscope, said viewing adaptor comprising:
an optical splitter configured to:
receive images from said endoscope; and
divide said image toward a first port and a second port; and
an image capture device in communication with said first port, said image capture device configured to:
capture images of an area illuminated by said selected one of said light emitting diodes of said plurality of lighting sources.

19. The body cavity treatment device of claim 18, wherein at least one of said first port and said second port comprises:
an emission filter, said emission filter configured to:
limit a wavelength range of light received to a known wavelength range.

20. The treatment device of claim 18, wherein said light therapy treatment device comprises:
an image capture device configured to:
capture images of an area illuminated by said selected one of said light emitting diodes of said plurality of lighting sources.

* * * * *